United States Patent [19]

Rizaev et al.

[11] 4,065,487

[45] Dec. 27, 1977

[54] PROCESS FOR PRODUCING BENZONITRILE

[76] Inventors: Ramiz Gasan Kuli ogly Rizaev, ulitsa Sharif-zade, 148, blok 5, kv. 67; Soltan Dzhafarovich Mekhtiev, ulitsa Khagani, 26/32, blok 5, kv. 92; Zemfira Jusif kyzy Magerramova, ulitsa E.Saratovtsa, 3/5, kv. 14; Viktor Efimovich Sheinin, ulitsa Pervomaiskaya, 251, blok 2, kv. 28; Mirabdulla Mirakhmed ogly Mirataev, ulitsa Khanlara, 24, kv. 24; Idris Aslan ogly Guseinov, Kirovsky raion, poselok Khodzhi Gasan, ulitsa A. Matrosova, 28, all of Baku, U.S.S.R.

[21] Appl. No.: 707,426

[22] Filed: July 21, 1976

[51] Int. Cl.$^2$ ............................................. C07C 120/14
[52] U.S. Cl. ................................. 260/465 C; 252/467
[58] Field of Search .................................... 260/465 C

[56] References Cited

U.S. PATENT DOCUMENTS 3,497,545  2/1970  Golden et al. ........................ 260/465

*Primary Examiner*—Dolph H. Torrence
*Attorney, Agent, or Firm*—Haseltine, Lake & Waters

[57] ABSTRACT

A process for producing benzonitrile which comprises reacting toluene with ammonia in the presence of oxygen or a mixture thereof with inert gases and a catalyst; as the latter use is made of a mixture of oxides of vanadium, chromium, antimony and bismuth taken in a molar ratio of 1–10:1–20:1–10: 1–15 respectively deposited onto a carrier. The process is effected at a temperature within the range of from 340° to 480° C, followed by isolation of the desired product.

The present invention makes it possible to substantially increase the output of benzonitrile from one liter of the catalyst per hour due to an increased capacity and selectivity of the catalyst.

3 Claims, No Drawings

PROCESS FOR PRODUCING BENZONITRILE

The present invention relates to processes for producing aromatic nitriles and, more specifically, to a process for producing benzonitrile which is useful as a starting material in the production of plastics, pharmaceutical compositions, surface-active compounds, synthetic dyes as well as selective solvents and intermediate products for the manufacture of corrosion-protective coatings.

Known in the art is a process for producing benzonitrile by way of reacting toluene with ammonia and oxygen in the presence of water taken in a molar ratio of 1:2-10:1.5-20:15-40, preferably 1:4.4:13:39 respectively, at a temperature ranging from 450° to 500° C using a catalyst consisting of a mixture of vanadium pentoxide and molybdenum oxide deposited onto alumina at a weight ratio of 99-75:1-25 respectively.

Specific surface area of alumina is 0.5 m²/g.

Weight supply rate of toluene is 0.06 g/l of the catalyst per hour.

Output of benzonitrile is 60 g/l of the catalyst per hour. Yield of benzonitrile is 91 mol.% as calculated on the toluene passed through the reactor.

This prior art process has a disadvantage residing in a low output of benzonitrile from a unit volume of the catalyst due to a low capacity of the latter as well as due to the use of considerable amounts of water which complicates the process technology.

It is an object of the present invention to increase the yield of benzonitrile.

This object is accomplished by that in the process for producing benzonitrile by reacting toluene with ammonia in the presence of oxygen or a mixture thereof with inert gases and a catalyst at a temperature within the range of from 340° to 480° C, followed by isolation of the desired product, in accordance with the present invention, as the catalyst use is made of a mixture of oxides of vanadium, chromium, antimony and bismuth taken in a ratio of 1-10:1-20:1-10:1-15 respectively deposited onto a carrier.

It is advisable to employ, as the carrier, alumina calcined at the temperature of 900° C or silica gel.

The process for producing benzonitrile according to the present invention is performed in the following manner.

Through a reactor charged with the catalyst a mixture of toluene, ammonia and oxygen taken in a molar ratio of 1:2-35:2-30 respectively is passed at a temperature ranging from 340° to 480° C.

Space rate of toluene supply is 0.10-0.35 hr⁻¹. The process should be preferably conducted at a temperature within the range of from 400° to 420° C at the space rate of toluene supply of 0.25 hr⁻¹ using a mixture of toluene, ammonia and air taken in the molar ratio of 1:5:40 respectively.

A vapour-gas mixture from the reactor is condensed, followed by isolation of the desired product, i.e. benzonitrile. The process is performed using a stationary or fluidized bed of a catalyst.

As the catalyst use is made of a mixture of oxides of vanadium, chromium, antimony and bismuth taken in a molar ratio of 1-10:1-20:1-10:1-15, preferably 1:3:3.5:2, respectively, applied onto a carrier, i.e. alumina calcined at the temperature of 900° C or silica gel. The mixture is applied onto the carrier at a weight ratio of 1-35:99-6.5, preferably 1:4.

The catalyst is prepared in the following manner.

To an acidic solution of ammonium metavanadate at a temperature within the range of from 50° to 60° C and progressive stirring appropriate ammounts of soluble salts of bismuth, antimony and chromium are added, whereafter the solution temperature is elevated to 90°-95° C and the carrier is added to the solution. At the above-mentioned temperature said solution is maintained for 5-6 hours and then vaporized. The residual mass comprising the carrier impregnated with salts of bismuth, antimony, chromium and vanadium is dried at a temperature within the range of from 150° to 200° C for a period of 3 to 4 hours and then calcined at a temperature of from 500° to 600° C in a current of dry air for a period of 10 to 15 hours to give a catalyst consisting of a mixture of oxides of vanadium, chromium, antimony and bismuth deposited onto the carrier.

The process for producing benzonitrile according to the present invention has certain advantages over the prior art processes which reside in that the use of a catalyst consisting of a mixture of oxides of vanadium, antimony, chromium and bismuth deposited onto a carrier makes it possible to increase the output of benzonitrile per liter of the catalyst per hour up to 228 g due to an increased capacity and selectivity of the catalyst. Absence of water considerably simplifies the process technology.

Due to an increased selectivity of the catalyst the amount of by-products is decreased and said by-products are readily separated from the desired product.

For a better understanding of the present invention some specific examples illustrating the process for producing benzonitrile are given hereinbelow.

EXAMPLE 1

Through a reactor with a fluidized bed of a catalyst a mixture of toluene, ammonia and oxygen taken in the molar ratio of 1:5:8 respectively is passed at the temperature of 420° C and space rate of toluene supply of 0.25 hr⁻¹.

The catalyst consists of a mixture of oxides of vanadium, chromium, antimony and bismuth taken in the molar ratio of 1:3:3.5:2 respectively deposited onto alumina calcined at the temperature of 900° C, at the weight ratio between the mixture of said oxides and the carrier equal to 1:4.

Conversion of toluene is 100%. The yield of benzonitrile, as calculated for the toluene passed through the reactor, is 95.4 mol.%. The output of benzonitrile is 228 g/l of the catalyst per hour.

EXAMPLE 2

Through a reactor with a fluidized bed of a catalyst a mixture of toluene, ammonia and oxygen taken in the molar ratio of 1:10:20 respectively is passed at the temperature of 380° C and space rate of toluene supply of 0.25 hr⁻¹.

The catalyst is similar to that described in the foregoing Example 1.

The vapour-gas mixture effluent from the reactor is condensed, followed by isolation of the desired product.

Conversion of toluene is 75.8%. The yield of benzonitrile, as calculated for the toluene passed through the reactor, is 73.7 mol.%. The output of benzonitrile is 177 g/l of the catalyst per hour.

EXAMPLE 3

Through a reactor with a fluidized bed of a catalyst a mixture of toluene, ammonia and air taken in the molar ratio of 1:4:20 respectively is passed at the temperature of 360° C and space rate of toluene supply of 0.25 hr$^{-1}$.

The catalyst consists of a mixture of oxides of vanadium, chromium, antimony and bismuth taken in the molar ratio of 1:10:5:15 respectively deposited onto alumina at the weight ratio between the oxide mixture and the carrier equal to 1:9.

The vapour-gas mixture effluent from the reactor is condensed and the desired product is then separated therefrom. The yield of benzonitrile, as calculated for the toluene passed through the reactor, is 52.5 mol.%. Conversion of toluene is 70%. The output of benzonitrile is 117 g/l of the catalyst per hour.

EXAMPLE 4

Through a reactor with a stationary bed of a catalyst a mixture of toluene, ammonia and oxygen taken in the molar ratio of 1:20:5 respectively is passed at the temperature of 340° C and space rate of toluene supply of 0.15 hr$^{-1}$.

The catalyst is similar to that described in the foregoing Example 1.

The vapour-gas mixture effluent from the reactor is condensed and the desired product is then isolated. Conversion of toluene is 60%. The yield of benzonitrile, as calculated for the toluene passed through the reactor, is 59.1 mol.%. The output of benzonitrile is 85 g/l of the catalyst per hour.

EXAMPLE 5

Through a reactor with a fluidized bed of a catalyst a mixture of toluene, ammonia and oxygen taken in the molar ratio of 1:5:8 respectively is passed at the temperature of 440° C and space rate of toluene supply of 0.25 hr$^{-1}$.

The catalyst is similar to that described in Example 1 hereinbefore.

The vapour-gas mixture leaving the reactor is condensed and the desired product is then isolated.

Toluene conversion is 100%. The yield of benzonitrile, as calculated on the toluene pass through the reactor, is 88.1 mol.%. The output of benzonitrile is 212 g/l of the catalyst per hour.

EXAMPLE 6

Through a reactor with a stationary bed of a catalyst a mixture of toluene, ammonia and oxygen taken in the molar ratio of 1:25:15 respectively is passed at the temperature of 380° C and space rate of toluene supply of 0.25 hr$^{-1}$.

The catalyst consists of a mixture of oxides of vanadium, chromium, antimony and bismuth taken in the molar ratio of 5:2:7:3 respectively deposited onto silica gel at the weight ratio between the oxide mixture and the carrier equal to 1:3. Toluene conversion is 87%.

The yield of benzonitrile, as calculated for the toluene passed through the reactor, is 80.9 mol.%. The output of benzonitrile is 194 g/l of the catalyst per hour.

EXAMPLE 7

Through a reactor with a stationary bed of a catalyst a mixture of toluene, ammonia and air taken in the molar ratio of 1:5:25 respectively is passed at the temperature of 480° C and space rate of toluene supply of 0.25 hr$^{-1}$.

The catalyst consists of a mixture of oxides of vanadium, chromium, antimony and bismuth taken in the molar ratio of 1:1:3:15 respectively applied onto silica gel at the weight ratio between the oxide mixture and the carrier equal to 1:24.

The vapour-gas mixture leaving the reactor is condensed and the desired product is then isolated. Toluene conversion is 100%.

The yield of benzonitrile, as calculated for the toluene passed through the reactor, is 55.0 mol.%. The output of benzonitrile is 132 g/l of the catalyst per hour.

EXAMPLE 8

Through a reactor with a fluidized bed of a catalyst a mixture of toluene, ammonia and oxygen taken in the molar ratio of 1:5:8 respectively is passed at the temperature of 400° C and space rate of toluene supply of 0.25 hr$^{-1}$. The catalyst is similar to that described in Example 1 hereinabove.

The vapour-gas mixture from the reactor is condensed and the desired product is then isolated. Conversion of toluene is 95%. The yield of benzonitrile, as calculated for the toluene passed through the reactor, is 91.7 mol.%. The output of benzonitrile is 219 g/l of the catalyst per hour.

EXAMPLE 9

Through a reactor with a fluidized bed of a catalyst a mixture of toluene, ammonia and oxygen taken in the molar ratio of 1:10:10 respectively is passed at the temperature of 400° C and space rate of toluene supply of 0.25 hr$^{-1}$. The catalyst consists of a mixture of oxides of vanadium, chromium, antimony and bismuth taken in the molar ratio of 10:2:6:7 respectively deposited on alumina at the weight ratio of the mixture of said oxides to the carrier equal to 1:12. Conversion of toluene is 85%. The yield of benzonitrile, as calculated for the toluene passed through the reactor, is 75 mol.%. The output of benzonitrile is 176 g/l of the catalyst per hour.

EXAMPLE 10

Through a reactor with a fluidized bed of a catalyst a mixture of toluene, ammonia and oxygen taken in the molar ratio of 1:12:8 respectively is passed at the temperature of 440° C and space rate of toluene supply of 0.25 hr$^{-1}$. The catalyst consists of a mixture of oxides of vanadium, chromium, antimony and bismuth taken in the molar ratio of 1:20:3:1 respectively deposited onto alumina at the weight ratio between the mixture of said oxides and the carrier equal to 1:8.

Conversion of toluene is 100%. The yield of benzonitrile, as calculated for the toluene passed through the reactor, is 65 ml.%. The output of benzonitrile is 153 g/l of the catalyst per hour.

EXAMPLE 11

Through a reactor with a fluidized bed of a catalyst a mixture of toluene, ammonia and oxygen taken in the molar ratio of 1:20:15 respectively is passed at the temperature of 380° C and space rate of toluene supply of 0.25 hr$^{-1}$. The catalyst consists of a mixture of oxides of vanadium, chromium, antimony and bismuth taken in the molar ratio of 2:3:9:2 respectively deposited onto alumina at the weight ratio between the mixture of said oxides and the carrier equal to 1:6.

Conversion of toluene is 75%. The yield of benzonitrile as calculated for the toluene passed through the reactor, is 60 mol.%. The output of benzonitrile is 141 g/l of the catalyst per hour.

EXAMPLE 12

Through a reactor with a fluidized bed of a catalyst a mixture of toluene, ammonia and oxygen taken in the molar ratio of 1:8:22 respectively is passed at the temperature of 360° C and space rate of toluene supply of 0.25 hr$^{-1}$. The catalyst consists of a mixture of oxides of vanadium, chromium, antimony and bismuth taken in the molar ratio of 4:2:3:10 respectively deposited onto alumina, at the weight ratio between the mixture of said oxides and the carrier equal to 1:4.

The yield of benzonitrile, as calculated for the toluene passed through the reactor, is 50 mol.%. Conversion of toluene is 65%. The output of benzonitrile is 118 g/l of the catalyst per hour.

What is claimed is:

1. A process for producing benzonitrile comprising reacting toluene with ammonia at a temperature within the range of from 340° to 480° C in the presence of oxygen or a mixture thereof with inert gases and a catalyst, viz. a mixture of oxides of vanadium, chromium, antimony and bismuth taken in a molar ratio of 1-10:1-20:1-10:1-15 respectively deposited onto a carrier, followed by isolation of the desired product.

2. A process as claimed in claim 1, wherein the mixture of said oxides of vanadium, chromium, antimony and bismuth is employed in the molar ratio of the components of 1:3:3.5:2 respectively, said mixture being applied onto a carrier.

3. A process as claimed in claim 1, wherein use is made of a catalyst deposited onto a carrier selected from the group consisting of silica gel and alumina calcined at the temperature of 900° C.

* * * * *